United States Patent [19]

Chupp

[11] Patent Number: 4,662,742
[45] Date of Patent: May 5, 1987

[54] SCATTER/FLUORESCENE BEAM SPLITTER IN A FLOW CYTOMETRY APPARATUS

[75] Inventor: Vernon Chupp, Los Altos, Calif.

[73] Assignee: Becton, Dickinson and Company, Franklin Lakes, N.J.

[21] Appl. No.: 732,765

[22] Filed: May 10, 1985

[51] Int. Cl.⁴ .................... G01N 33/48; G01N 21/64
[52] U.S. Cl. ........................................ 356/39; 356/73
[58] Field of Search ............ 356/73, 39, 318, 335–339, 356/343, 364; 250/461.2, 461.1, 573–575; 350/394; 435/29

[56] References Cited

U.S. PATENT DOCUMENTS

| | | | |
|---|---|---|---|
| 3,603,689 | 9/1971 | Shelnutt | 356/364 X |
| 3,704,933 | 12/1972 | Buchan | 350/394 X |
| 3,901,602 | 8/1975 | Gravatt | 356/364 X |
| 3,966,302 | 6/1976 | Mikoda et al. | 350/334 |
| 4,500,641 | 2/1985 | Engh et al. | 435/29 X |

Primary Examiner—Vincent P. McGraw
Attorney, Agent, or Firm—Richard J. Rodrick

[57] ABSTRACT

A flow cytometry apparatus for determining one or more characteristics of particles or the like flowing in a liquid stream includes a nozzle for generating a liquid flow stream for moving particles therethrough substantially one at a time. A light source provides a beam of light to illuminate the particles moving in the stream. An optical path for light scattered and fluorescence emitted by each moving particle has an axis which preferably makes a 90° angle with respect to the axis of the illuminating beam. A beam splitter is positioned in this optical path with an angle of incidence greater that 45° so as to transmit fluorescence and to reflect light scatter. Detectors are provided for detecting the transmitted fluorescence and the reflected light scatter and for associating the scattered light and fluorescence with one or more characteristics of each particle.

10 Claims, 3 Drawing Figures

SCATTER/FLUORESCENE BEAM SPLITTER IN A FLOW CYTOMETRY APPARATUS

BACKGROUND OF THE INVENTION

1. Field of the Invention

The present invention relates to a flow cytometry apparatus, and more particularly, concerns a flow cytometry apparatus for determining one or more characteristics of cells or the like which includes improved optics for wide angle light scatter and fluorescence detection.

2. Description of the Prior Art

Flow cytometry apparatuses rely upon the flow of cells or other particles in a liquid flow stream in order to determine one or more characteristics of the cells under investigation. For example, a liquid sample containing cells is directed through the flow cytometry apparatus in a rapidly moving liquid stream so that each cell passes serially, and substantially one at a time, through a sensing region. Cell volume may be determined by changes in electrical impedance as each cell passes through the sensing region. Similarly, if an incident beam of light is directed at the sensing region, the passing cells scatter such light as they pass therethrough. This scattered light has served as a function of cell shape, index of refraction, opacity, roughness and the like. Further, fluorescence emitted by labeled cells which have been excited as a result of passing through the excitation energy of the incident light beam is detectable for identification of specifically labeled cells. Not only is cell analysis performed on the flow cytometry apparatuses, but sorting of cells may also be achieved. Lasers have been used as the source of the incident beam of illumination in flow cytometry apparatuses, as well as sources of incoherent and non-collimated light, such as mercury or xenon arc lamps.

In most of the presently known and available flow cytometry apparatuses, fluorescence emitted by the cells is typically collected at an angle whose viewing axis is 90° relative to the axis of light excitation. In addition, wide angle light scatter, typically at 90°, has been found to obtain information about cells relating to shape and internal morphology. Inasmuch as both light scatter and fluorescence at 90° may be collected with the same optical collection system, filters or light beam separators have been utilized to split the 90° fluorescence and light scatter so that each may be detected separately. Furthermore, for most efficient collection, and if the incident light beam is provided by a laser, the light beam is typically polarized with the electric vector oriented normal to the plane containing the 90° angle defined by the excitation and collection axes.

It is a property of scattering, that light scattered at right angles from the incident beam retains its polarization. On the other hand, the polarization of fluorescence depends upon the molecules themselves, and not upon the incident light beam. In practice, however, fluorescence from most cells is usually modestly unpolarized.

At present, dichroic filters are employed in separating a light beam having both fluorescence and scatter components. Such filters frequently do not transmit fluorescence as efficiently as would be desirable. Additionally, dichroic filters are typically wavelength dependent. For instance, changing the excitation wavelength from one frequency to another would require a different dichroic filter. It is also expensive to fabricate these types of dichroic filters.

In some instances, dielectric broadband filters have been employed to separate the light scatter and fluorescence components of a light beam. Such broadband filters normally do not have polarization benefits. In other words, and for example, reflecting 25% of the scatter would imply transmitting only 75% of the fluorescence.

It has also been known to employ uncoated glass or quartz as a beam splitter plate in a flow cytometry apparatus. Such a glass plate has typically been positioned at a 45° angle relative to the incident light beam comprising both light scatter and fluorescence components. At the 45° angle, fluorescence is transmitted efficiently, but light scatter is reflected rather inefficiently.

Many different flow cytometry apparatuses and techniques have been described in a review article by John A. Steinkamp, entitled "Flow Cytometry," *Review of Scientific Instruments* 55 (9), September 1984. While there are a variety of different approaches for optically sensing the characteristics of cells, there is still a need for further improvements in such optics so that cellular information may be obtained more efficiently and reliably.

SUMMARY OF THE INVENTION

The flow cytometry apparatus of the present invention for determining one or more characteristics of particles or the like flowing in a liquid stream comprises means for moving particles, substantially one at a time, in a liquid flow stream. Means provides a plane polarized beam of light to illuminate the particles moving in the stream. Beam splitter means is positioned in the collected beam light path so that light scattered and fluorescence emitted by each moving particle are directed thereto. The splitter means is oriented at an incidence angle greater than 45°, preferably approaching Brewster's angle, so as to transmit fluorescence and to reflect light scatter. Means for detecting the transmitted fluorescence and the reflected light scatter related to each particle is included, which also associates the detected scattered light and fluorescence with one or more characteristics of such particle.

In a preferred embodiment of the present invention, the source for providing an incident beam of linearly polarized light is a laser, which also provides excitation energy to cause fluorescently labeled cells in the flow stream to emit fluorescence. The preferred apparatus includes a light scatter detector and a fluorescence detector which respectively detects light scattered and fluorescence emitted by each moving cell at substantially 90° relative to the axis of the laser beam. A beam splitter is positioned in the light path between the cells and the detectors so that both light scatter and fluorescence at substantially 90° are directed to the beam splitter. It is preferred that the beam splitter be oriented at its Brewster's angle relative to the incident light scatter and fluorescence to transmit fluorescence and to reflect light scatter.

In accordance with the principles of the present invention, improved optics are provided to split the light scatter/fluorescence beam, particularly for wide angle detection of such light-related information about the cells moving through the flow cytometry apparatus. The present invention is particularly advantageous if both light scatter and fluorescence are to be collected with the same optical collection system. Use of a preferably uncoated flat plate of glass at a wide incidence angle, such as at Brewster's angle, with the plane of incidence normal to the electric vector of the laser beam, serves as an ideal beam splitter. A very high percentage of unpolarized fluorescence is transmitted through the beam splitter of the present invention, while an effective percentage of light scatter is reflected off the beam splitter so that such light scatter may be detected. Furthermore, the present invention employs such a beam splitter without the reliance upon dichroic filters or dielectric broadband filters.

Accordingly, the present beam splitter is straightforward and economical to fabricate, and is modestly independent of excitation wavelength. In addition, the beam splitter may be oriented at an optimum angle of incidence so as to balance the loss in fluorescence with the gain in scatter to thereby obtain the best efficiency for both light scatter and fluorescence detection. A number of other advantages, in addition to the aforementioned significant advantages, are offered by the present invention as will become more apparent from a reading the the detailed description set forth below.

BRIEF DESCRIPTION OF THE DRAWINGS

FIG. 1 is a schematic illustration of a preferred embodiment of the optical elements and light paths of a flow cytometry apparatus of the present invention for determining one or more characteristics of cells or the like;

DETAILED DESCRIPTION

Figure 1:
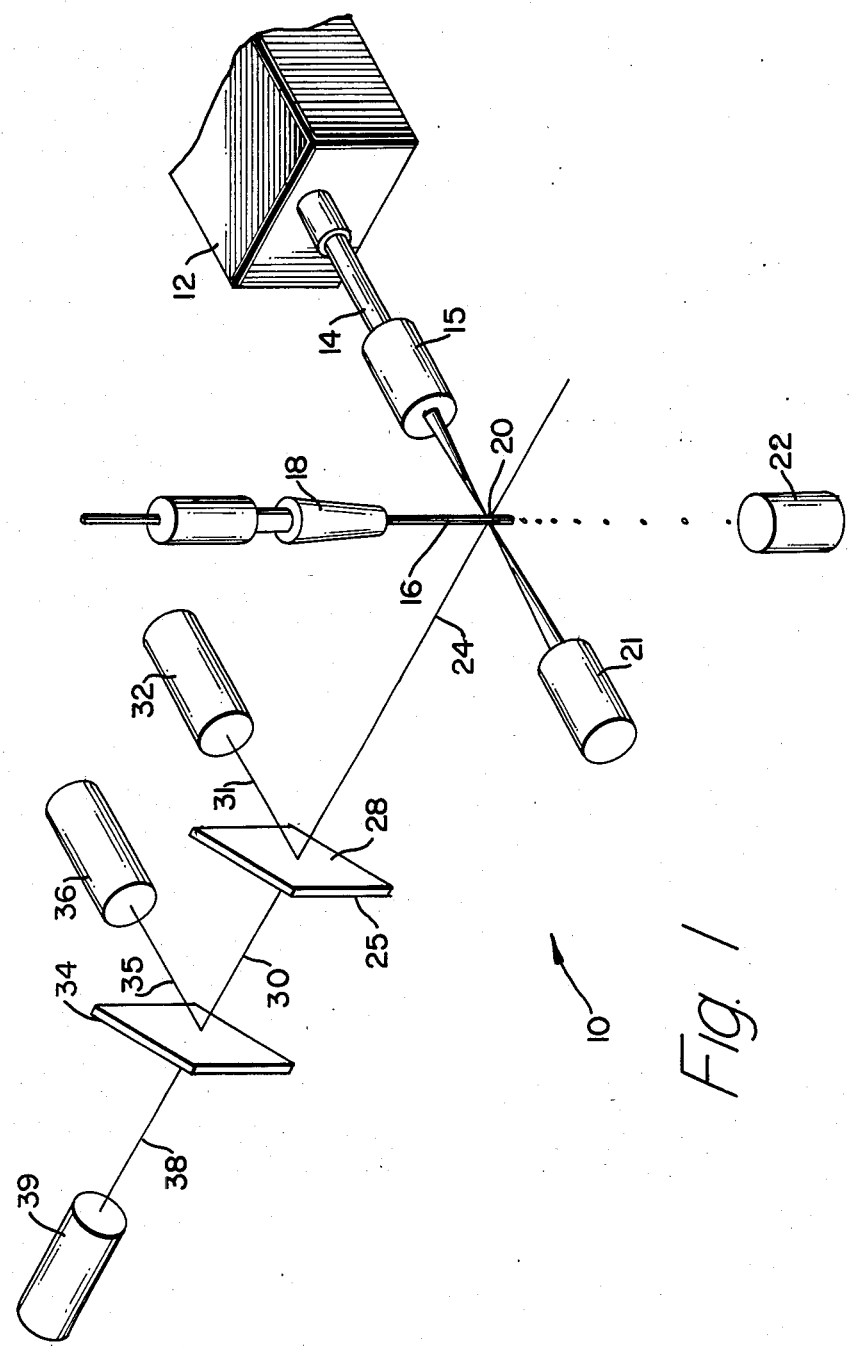

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, and FIG. 1 in particular, the optical and particle flow elements of a flow cytometry apparatus 10 are illustrated. The optical and flow elements of FIG. 1 represent the major components of a flow cytometry apparatus for moving particles, such as cells or the like, in a liquid stream, substantially one at a time, in order to assess those particles for specific characteristics thereof. For example, the elements of the device of FIG. 1 may be included in a FACS ™ fluorescence-activated cell sorter, manufactured and sold by Becton Dickinson Immunocytometry Systems, Mountain View, Calif. The FACS cell sorter analyzes and sorts cell populations on the basis of light scatter and fluorescence in a wide variety of research laboratory applications. In addition to the optical and flow elements to be described in more particular detail herein, and which may be embodied in an instrument such as the FACS cell sorter, other details of a cell sorting apparatus useful in conjunction with the present invention are described in U.S. Pat. No. 3,826,364. It is understood that the present invention is useful in many different types of flow cytometry or flow fluorometric apparatuses, whether measuring light scatter, particle volume, fluorescence or other optical parameters for the identification or quantification of cells or the like in a sample liquid medium. The optical elements, in particular, of the present invention represent the essence of the improvement in flow cytometry apparatuses such as described in the aforementioned patent.

As illustrated in FIG. 1, light energy is provided for the present flow cytometry apparatus by a light source 12 such as a laser which provides a linearly polarized collimated beam of light at a singular wavelength or at a number of discreet wavelengths. Alternatively, light source 12 may be broad-spectrum arc lamp, such as mercury or xenon, with polarizing means included in excitation light path 14a produced by light source 12. Typically, apparatus 10 also includes a lens 15 which focuses the light beam at a liquid stream 16 containing the particles or cells under investigation.

A nozzle 18, incorporated within the flow cytometry apparatus of the present invention, facilitates the flowing of cells or particles within liquid stream 16. The utilization of a nozzle of this type is well-known and is described, for example, in U.S. Pat. No. 3,826,364. Nozzle 18 provides a hydrodynamically focused flow of cells within a sheath fluid, the sheath fluid and cells comprising liquid flow stream 16. As each cell or particle passes through the focused light region 20, where light beam 14 intersects liquid stream 16, light scattered thereby may be detected. An appropriate photodetector 21, as illustrated in FIG. 1, is positioned to receive light scattered forwardly by each cell. Before describing the elements associated with the detection of fluorescence and wide angle light scatter, it should be pointed out that the particles in liquid stream 16 may be collected in an appropriate container 22, or, perhaps, may be sorted and collected in different containers if the flow cytometry apparatus employs a sorting capability.

Fluorescence, if emitted by cells energized by the illumination from the light source, may also be detected. Similarly, light scattered in different directions, besides the forward direction, may be detected. In laser excited flow cytometry, both fluorescence and wide angle light scatter are typically collected at an angle whose viewing axis is 90° relative to the excitation axis of light beam 14. In FIG. 1, axis 24 represents the 90° viewing access for the collection of fluorescence and wide angle scatter. Thus, light traveling along axis 24, for purposes of the ensuing discussion, includes both light scatter and fluorescence as its components.

In order to collect fluorescence and light scatter at the 90° angle from the incident laser beam, the light scatter and fluorescence should be separated or split. To accomplish such splitting without relying upon the presently used dichroic filters, a beam splitter plate 25 is utilized by the present invention. Beam splitter 25 functions to receive both scattered light and fluorescence at the 90° angle and to re-direct each such component in different directions. Such re-direction of light scatter and fluorescence then permits each of the light scatter and fluorescence to be collected separately, even though both originate at the 90° angle.

Figure 2:
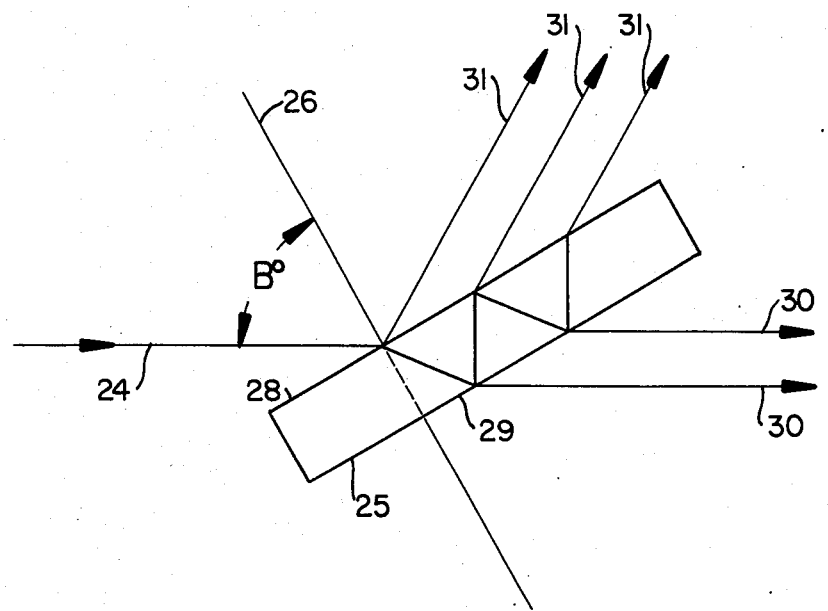
FIG. 2 is an enlarged schematic representation of the preferred angularly oriented, scatter/fluorescence beam splitter of the present invention.

Specifically, beam splitter 25 is intended to transmit fluorescence and to reflect light scatter. To this end, the beam splitter is positioned along axis 24 so that it is angularly oriented relative to axis 24. This angle normally referred to as the angle of incidence is designated as angle B in FIG. 2 and is the angle between axis 24 and a vector 26 which is a line extending normal to the surface 28 of beam splitter 25. For best results in accordance with the present invention, angle B should be greater than 45°. Preferably, angle B is the Brewster's angle of the beam splitter plate. As is well-known in the optical field, Brewster's angle represents the angle of incidence at which the amount of reflectance is minimized for light polarized parallel to the plane of incidence. Thus, at such angle of incidence, there would be little or no reflection loses. Brewster's angle is, moreover, a function of the material out of which beam splitter 25 is fabricated. When angularly oriented as illustrated in FIG. 2, light traveling along axis 24, comprised of light scatter and fluorescence, is split into two beams. Fluorescence, which consists of both polarization vectors, is efficiently transmitted through beam splitter 25 and travels along the axis represented by arrows 30. On the other hand, scattered light consists only of the polarization vector which has a reflectance component at Brewster's angle, and is thus represented by arrows 31. Once light scatter and fluorescence have been separated, each may be collected by appropriate photodetectors.

For example, the reflected light scatter may be collected in photodetector 32 as illustrated in FIG. 1. Before the transmitted fluorescence traveling along axis 30 is collected, the fluorescence signal may be further refined. If the transmitted fluorescence includes a number of different color regions, a dichroic mirror 34 may be utilized to separate the different color wavelengths. Thus, and for example, fluorescence in the green color region may be reflected by dichroic mirror 34 along axis 35 and collected in an appropriate photodetector 36. On the other hand, fluorescence in the red color region may be transmitted through dichroic mirror 34 along axis 38 and collected in an appropriate photodetector 39. While not illustrated in FIG. 1, those skilled in the art will appreciate that various lenses, filters, barriers or the like may be employed in conjunction with each of the photodetectors to obtain as pure a signal as possible. Obtaining such optically clean signals is most desirable particularly when a four-parameter sensing apparatus (two fluorescence channels and two light scatter channels) is utilized, such as the apparatus illustrated in FIG. 1.

Referring once again to FIG. 2, it can be seen that both surfaces 28 and 29 of beam splitter 25 have been used to reflect and transmit light scatter and fluorescence, respectively. In order to effectively use both surfaces of the beam splitter for the transmission and reflectance properties, it is preferred that beam splitter 25 be a thin, uncoated flat plate. For example, a beam splitter having a thickness range of 1 to 2 mm has been found to perform effectively in the present invention.

While different materials may be chosen for the beam splitter, having the capability of reflecting light scatter and transmitting fluorescence, particularly when unpolarized, commonly available low cost glasses are most desirable. In particular, a borosilicate glass, sold under the trade name Pyrex, has been found to be most suitable for the present invention. A thin, flat, polished piece of borosilicate glass provides a beam splitter that transmits substantially more than 75% of the unpolarized fluorescence which strikes the splitter. This same borosilicate glass beam splitter reflects an amount of scattered light so as to obtain a signal which may be adequately detected. For borosilicate glass, Brewster's angle occurs at approximately 56°. Thus, in FIG. 2, angle B, when beam splitter 25 is made from borosilicate glass, would be at approximately 56° to obtain the results in accordance with the present invention.

Figure 3:
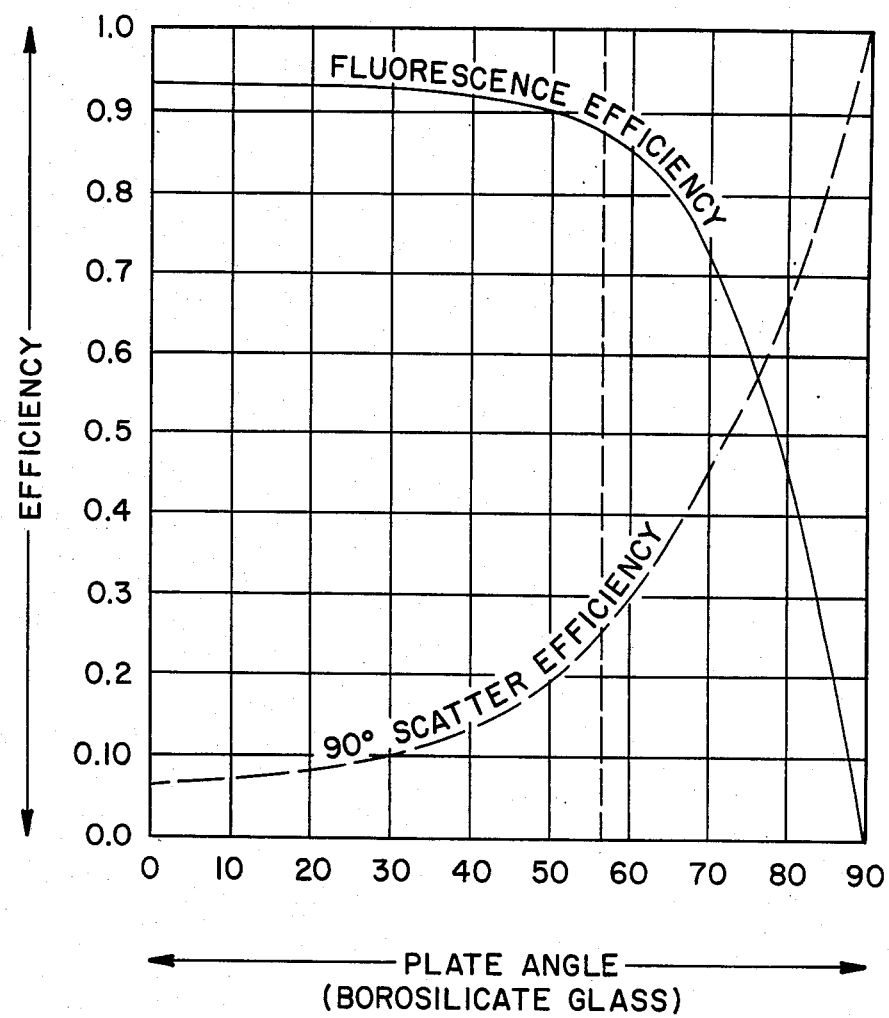
FIG. 3 is a graphic representation of the efficiency characteristics of the present beam splitter depicting 90° light scatter and fluorescence as parameters.

It should be pointed out that the angle at which beam splitter 25 is oriented along axis 24 typically represents a trade-off between the efficiencies of fluorescence transmission and light scatter reflectance. Assuming the fluorescence to be unpolarized, reference to FIG. 3 illustrates the efficiencies of fluorescence transmission and light scatter reflectance at 90° as a function of beam splitter plate angle. As the incident angle of the plate increases, the fluorescence efficiency decreases and the scatter efficiency increases. Therefore, choosing the optimum angle of incidence is a matter of balancing the loss in fluorescence with gain in scatter. Since scattering is a far more efficient process than fluorescence, the angle should be increased only to the point where the loss in fluorescence is substantially undetectable in terms of signal-to-noise performance. For example, by increasing the incidence angle from 45° to Brewster's angle (seen in FIG. 3 as approximately 56°), the fluorescence efficiency only decreases by about 4%, an amount so small as to be substantially undetectable in terms of signal-to-noise. At the same time, the scatter efficiency is increased nearly 60%. If the plate angle is further increased to 65°, for example, the fluorescence efficiency is decreased by about 11%, which starts to become noticeable in terms of fluorescence sensitivity. Therefore, at the Brewster's angle for borosilicate glass, the beam splitter of the present invention transmits approximately 88% of the unpolarized fluorescence and reflects approximately 25% of the available light scatter at 90°. These efficiencies are quite satisfactory in collecting the respective fluorescence and light scatter signals.

Once the above-described photodetectors receive the scatter and fluorescence signals, the information gained thereby may be further utilized. The various photodetectors may be well-known photomultiplier tubes or similar devices which convert light signals into electrical impulses so that the light thereby detected may be associated with the cells flowing through the apparatus. The electrical signals from the photodetectors are typically fed to the electronics (not shown) of the apparatus for purposes of display, storage or further processing so that one or more characteristics of the cells under analysis may be determined.

Thus, the present invention provides a scatter/fluorescence beam splitter for a flow cytometry apparatus which is particularly useful for wide angle light scatter and fluorescence detection. Particularly when the present beam splitter is oriented at a wide incidence angle, such as its Brewster's angle, a simple, economical light filter is provided.

What is claimed is:

1. A flow cytometry apparatus for determining characteristics of cells or the like flowing in a liquid stream comprising:
   means for moving cells, substantially one at a time, in a liquid flow stream;
   means for providing an incident beam of plane polarized illumination directed at the cells in said flow stream;
   means for collecting light scattered by each moving cell at substantially 90° relative to the axis of said incident beam;
   means for collecting fluorescence emitted by each moving cell at substantially 90° relative to the axis of said incident beam;

a substantially wavelength-independent beam splitter positioned relative to the axis of said incident beam so that both light scatter and fluorescence at substantially 90° are directed thereto, said splitter being oriented substantially at its Brewster's angle relative to the incident 90° light scatter and fluorescence to transmit unpolarized fluorescence and to reflect light scatter; and means for using said transmitted fluorescence and said reflected light scatter to determine one or more characteristics of said cells.

2. The apparatus of claim 1 wherein said means for providing said beam of illumination is a source of coherent light.

3. The apparatus of claim 2 wherein said source of coherent light is a laser.

4. The apparatus of claim 1 wherein said splitter is capable of transmitting more than about 75% of the unpolarized fluorescence which strikes said splitter.

5. The apparatus of claim 1 wherein said splitter is an uncoated, substantially flat, polished piece of glass.

6. The apparatus of claim 5 wherein said splitter is made from borosilicate glass.

7. The apparatus of claim 6 wherein Brewster's angle for borosilicate glass is approximately 56° and said splitter is oriented at approximately 56° relative to the incident light scatter and fluorescence.

8. A flow cytometry apparatus for determining one or more characteristics of particles or the like flowing in a liquid stream comprising:

means for moving particles, substantially one at a time, in a liquid flow stream;

means for providing a plane polarized beam of light to illuminate said particles moving in said stream;

a substantially wavelength-independent beam splitter means positioned in the collected beam light path so that light scattered and fluorescence emitted by each moving particle are directed thereto, said splitter means being oriented at an incidence angle greater than 45° relative to the collection axis so as to transmit unpolarized fluorescence and to reflect light scatter; and means for detecting said transmitted unpolarized fluorescence and said reflected light scatter related to each particle and for associating said detected scattered light and fluorescence with one or more characteristics of said particle.

9. The apparatus of claim 8 wherein said beam splitter means is oriented substantially at its Brewster's angle.

10. A flow cytometry apparatus for determining characteristics of cells or the like flowing in a liquid stream comprising:

means for moving cells, substantially one at a time, in a liquid flow stream;

a laser for providing an incident beam of linearly polarized illumination directed at the cells in said flow stream and for providing excitation energy to cause fluorescently labeled cells in said flow stream to emit fluorescence;

a light scatter detector for detecting light scattered by each moving cell at substantially 90° relative to the axis of said laser beam;

a fluorescence detector for detecting fluorescence emitted by each moving cell at substantially 90° relative to the axis of said laser beam;

an uncoated, substantially flat, polished borosilicate glass beam splitter, substantially independent of excitation wavelength, positioned in the light path between the cells and said detectors so that both light scatter and fluorescence at substantially 90° are directed thereto at an incidence angle of approximately 56° relative to the incident light scatter and fluorescence so as to transmit more than about 75% of the unpolarized fluorescence and to reflect said polarized scattered light; and means for using said transmitted fluorescence and said reflected light scatter to determine one or more characteristics of said cells.

* * * * *